(12) United States Patent
Chalupper (10) Patent No.: US 11,478,640 B2
(45) Date of Patent: Oct. 25, 2022

(54) FITTING DEVICE FOR BIMODAL HEARING STIMULATION SYSTEM

(71) Applicant: ADVANCED BIONICS AG, Staefa (CH)

(72) Inventor: Josef Chalupper, Paunzhausen (DE)

(73) Assignee: Advanced Bionics AG, Staefa (CH)

( * ) Notice: Subject to any disclaimer, the term of this patent is extended or adjusted under 35 U.S.C. 154(b) by 392 days.

(21) Appl. No.: 16/496,369

(22) PCT Filed: Mar. 23, 2017

(86) PCT No.: PCT/EP2017/056990
§ 371 (c)(1),
(2) Date: Sep. 20, 2019

(87) PCT Pub. No.: WO2018/171885
PCT Pub. Date: Sep. 27, 2018

(65) Prior Publication Data
US 2021/0106827 A1 Apr. 15, 2021

(51) Int. Cl.
*A61N 1/36* (2006.01)
*H04R 25/00* (2006.01)

(52) U.S. Cl.
CPC ......... *A61N 1/36039* (2017.08); *H04R 25/70* (2013.01)

(58) Field of Classification Search
CPC .............................. A61N 1/36039; H04R 25/70
See application file for complete search history.

(56) References Cited

U.S. PATENT DOCUMENTS

| | | | | |
|---|---|---|---|---|
| 2005/0245991 A1* | 11/2005 | Faltys | ................... | H04R 25/70 607/57 |
| 2012/0109006 A1* | 5/2012 | James | ................ | A61N 1/36039 600/559 |
| 2012/0230502 A1* | 9/2012 | Nishizaki | ............... | H04R 25/70 381/60 |
| 2013/0004000 A1 | 1/2013 | Franck | | |

(Continued)

FOREIGN PATENT DOCUMENTS

| WO | 2011032021 | 3/2011 |
|---|---|---|
| WO | 2012056427 | 5/2012 |

(Continued)

OTHER PUBLICATIONS

International Search Report and Written Opinion received in International Application No. PCT/US17/56990.

*Primary Examiner* — Rex R Holmes
*Assistant Examiner* — Jennifer L Ghand
(74) *Attorney, Agent, or Firm* — ALG Intellectual Property, LLC (57) ABSTRACT

There is provided a fitting device configured to be communicatively connected to first stimulation device comprising an implantable electric stimulation device including a plurality of stimulation channels for electrical stimulation of a patient's ipsilateral ear at various stimulation sites according to a electrical stimulation signal and a second stimulation device selected from the group consisting of a device for acoustic stimulation of the patient's ipsilateral ear and a device for acoustic stimulation of the patient's contralateral ear according to an acoustic stimulation signal for adjusting the first stimulation device and the second stimulation device.

20 Claims, 9 Drawing Sheets

(56) References Cited

U.S. PATENT DOCUMENTS

| | | | |
|---|---|---|---|
| 2014/0275730 A1 | 9/2014 | Lievens | |
| 2015/0215710 A1* | 7/2015 | Francart | A61N 1/36039 |
| | | | 381/326 |
| 2016/0175591 A1* | 6/2016 | Chalupper | A61B 5/16 |
| | | | 607/3 |
| 2018/0288541 A1* | 10/2018 | Chalupper | H04R 29/008 |

FOREIGN PATENT DOCUMENTS

| WO | 2015000528 | 1/2015 |
|---|---|---|
| WO | 2015018457 | 2/2015 |

\* cited by examiner

FITTING DEVICE FOR BIMODAL HEARING STIMULATION SYSTEM

The invention relates to a fitting device for a bimodal hearing stimulation system.

Typically, bimodal stimulation system combine neural stimulation, e.g. by a cochlear implant, and acoustic (i.e. vibrational) stimulation. Cochlear implants comprise an electrode array for electrical stimulation of the cochlear at various stimulation sites determined by the position of the respective electrode. Typical systems for bimodal stimulation of the hearing comprise a cochlear implant at the ipsilateral ear and a device for acoustic stimulation of the ipsilateral ear or the contralateral ear. Systems with electric and acoustic stimulation of the same ear are also known as hybrid devices or EAS devices. In systems with contralateral acoustic stimulation the acoustic stimulation device typically is an (electro-acoustic) hearing aid; alternatively, acoustic stimulation can be achieved by a bone conduction hearing aid.

For fitting a bimodal stimulation device a fitting device is connected to the electric stimulation device and the acoustic stimulation device in order to adjust the respective stimulation parameters individually so as to optimize the hearing impression of the patient. In a relatively simple model, the impact of the stimulation parameters may be described by the input/output (I/O) curves of the electric stimulation and the acoustic stimulation. For acoustic stimulation, the I/O curve represents the output level provided by the loudspeaker as the function of the input sound level at the microphone; the acoustic stimulation I/O curves vary as a function of the frequency (or the frequency band) of the audio signal (in a hearing instrument, the input audio signals are divided into various frequency channels for further signal processing). For electrical stimulation, the I/O curves represent the stimulation current for each stimulation channel (e.g. for each stimulation electrode) as a function of the input sound level at the microphone.

A fitting device typically has a graphical user interface which allows the audiologist to see the characteristic audiometric data of the patient, such as the hearing threshold level and the most comfortable level for various stimulation frequencies (such audiogram representation is typically used for fitting of acoustic stimulation devices, such as hearing aids) and allows the audiologist to manually adjust the stimulation parameters, such as the I/O curves of the acoustic stimulation for the patient, thereby individually optimizing the respective aided threshold and most comfortable levels.

For electrical stimulation the fitting device typically uses a representation in the graphical user interface which is different from that of a fitting device for a hearing aid; in particular, the graphical user interface of a fitting device for electrical stimulation typically shows the stimulation currents for each electrode which correspond to the hearing threshold level and/or the most comfortable level.

Further, the workflows for fitting of acoustic stimulation devices and for fitting electric stimulation devices typically are very different, so that usually an audiologist in a clinic where CI devices and bimodal stimulation devices are implanted is not familiar with the fitting of acoustic stimulation devices.

Thus, the fitting of bimodal hearing systems, both for ipsi- and contralateral stimulation, is counterintuitive, difficult-to-use and inefficient for the audiologist. A consequence for the patient is that the patient often will not receive the optimum individual fitting with bimodal systems.

WO 2012/056427 A9 relates to a method of fitting a bimodal system, wherein the fitting device comprises a graphical user interface which shows for each acoustic stimulation channel the aided hearing threshold level and the aided most comfortable level in dB SPL (sound pressure level), while for each electric stimulation channel the aided hearing threshold level and the aided most comfortable level are shown in electric level current units; the acoustic stimulation channels and the electric stimulation channels are shown in a common representation. The graphical user interface allows the audiologist to adjust the respective aided levels shown in the graphical interface in order to adjust the I/O curves of the bimodal device.

It is an object of the invention to provide for a fitting device for bimodal hearing stimulation systems which allows for fitting of both the neural stimulation device and the vibrational stimulation device in a convenient and easy-to-understand manner. It is a further object to provide for a corresponding fitting method.

According to the invention, these objects are achieved by a system as defined in claim 1 and a method as defined in claim 26.

The invention is beneficial in that, by allowing the user to select between a hearing aid (HA) type fitting mode and a cochlear implant (CI) type fitting mode, wherein each mode is suitable for fitting both stimulation devices, the user of the fitting device is enabled to select that type of fitting he or she is more familiar with, i.e. a hearing aid specialist may select the HA type fitting mode for fitting both the neural stimulation device and the vibrational stimulation device, and a CI specialist may select the CI-type fitting mode for fitting both the neural stimulation device and the vibrational stimulation device. Thereby an optimal fitting process may be achieved, irrespective of whether the user is a CI specialist or a hearing aid specialist. Optionally, a conventional fitting mode may be provided in addition for selection by the user, wherein a CI-type fitting mode is used for fitting of the neural stimulation device and a HA-type fitting mode is used for fitting the vibrational stimulation device.

Preferred embodiments of the invention are defined in the dependent claims.

Hereinafter, examples of the invention will be illustrated by reference to the attached drawings, wherein:

FIG. 7 is an example of a flow diagram for a conventional fitting mode;

Figure 1:
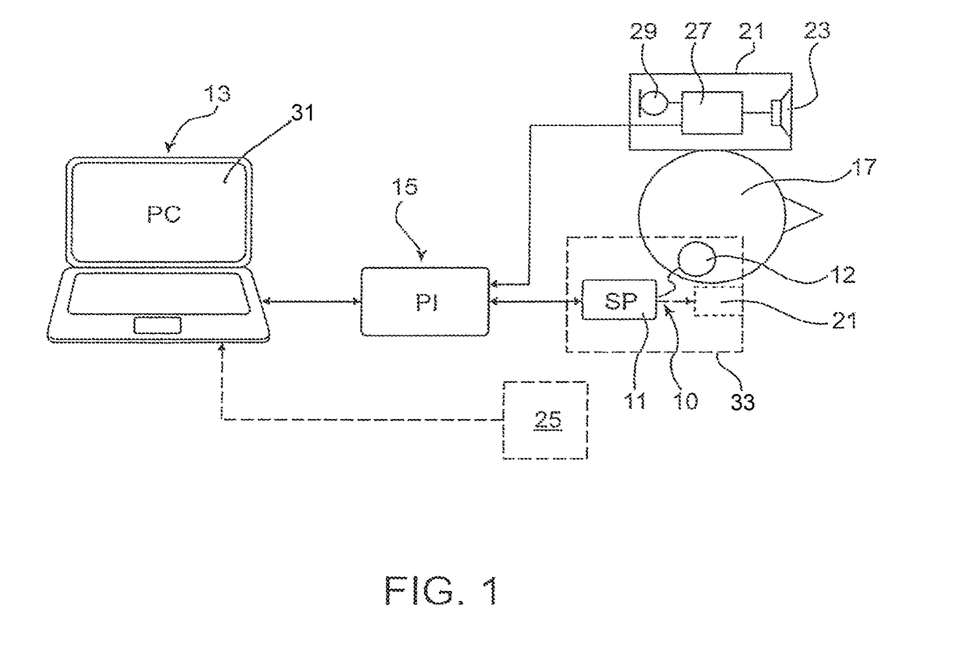
FIG. 1 is a schematic representation of an example of a system according to the invention.

FIG. 1 is a schematic representation of an example of a bimodal stimulation system according to the invention, comprising a fitting/programming unit 13, which may be implemented as a computer, a programming interface 15, a CI device 10 comprising a sound processing subsystem 11 and an implantable stimulation subsystem 12 and being worn by a patient 17 at the ipsilateral ear, and a hearing aid 21 worn at the contralateral ear and comprising a loudspeaker 23 for acoustic stimulation of the contralateral ear. The programming unit 13 communicates with the sound processing subsystem 11 and with the hearing aid 21 via the programming interface 15, which may be implemented as a wired or wireless connection (alternatively, there may be separate programming interfaces for electric. and acoustic stimulation).

The programming unit 13 serves to control the sound processing subsystem 11 of the CI device 10 such that probe neural stimulation signals may be applied to the ipsilateral ear of the patient 17 via the stimulation subsystem 12 and to control the hearing aid 21 such that probe acoustic stimulation signals may be presented via the loudspeaker 23 to the contralateral ear of the patient 17. Such probe stimulation signals may be presented separately (i.e. subsequently/independently) for acoustic and electric stimulation, or the probe stimulation signals may be presented for acoustic and electric stimulation in a synchronized manner. The perceptual behavioral response of the patient 17 to the such stimulation by internally generated probe stimulation signals is recorded by the programming unit 13 via a user interface, which may be part of the programming unit (such as the computer keyboard) or may be provided separately (as schematically indicated at 25 in FIG. 1), in order to be used in the fitting of the CI device 10 and the hearing aid 21, respectively, as will be explained below in detail.

In addition, the fitting unit 13 is configured to record the perceptual behavioral response of the patient 17 to stimulation by stimulation signals generated from audio signals captured by at least one microphone of the CI device 10 and/or the hearing aid 21. Such microphone-based stimulation signals may be generated by the CI device 10/hearing aid 21, or they may be generated by the fitting unit 13, or the CI device 10/hearing aid 21 may generate stimulation signals internally without the use of a microphone.

It is to be understood that the fitting unit 13 is used with the CI device 10 and the hearing aid 21 only for adjustment/fitting, but not during normal operation of the CI device 10 and the hearing aid 21.

In case that the fitting/programming unit 13 is adapted to generate audio signals/stimulation signals on its own, the programming interface 15 may be replaced by an audio interface for supplying the audio signals generated by the fitting/programming unit 13 to the CI device.

Figure 2:
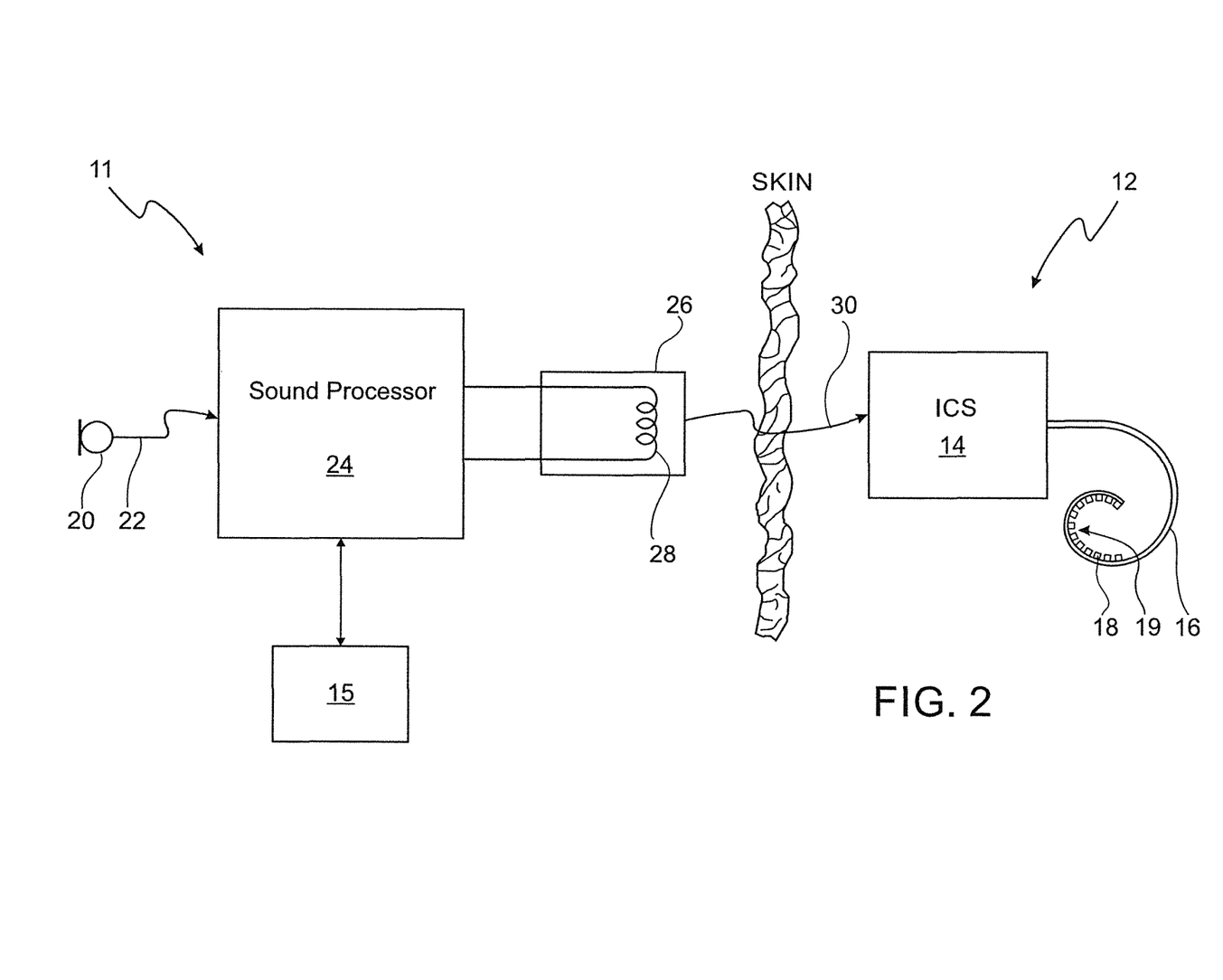
FIG. 2 is a schematic representation of an example of the CI device of FIG. 1.

In FIG. 2 an example of the cochlear implant device 10 of the system of FIG. 1 is shown schematically. The sound processing sub-system 11 serves to detect or sense an audio signal and divide the audio signal into a plurality of analysis channels, each containing a frequency domain signal (or simply "signal") representative of a distinct frequency portion of the audio signal. A signal level value is determined for each analysis channel by analyzing the respective frequency domain signal Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlear of a patient 17 in accordance with the stimulation parameters received from the sound processing sub-system 11. Electrical stimulation is provided to the patient 17 via a CI stimulation assembly 18 comprising a plurality of stimulation channels. The stimulation parameters may control various parameters of the electrical stimulation applied to a stimulation site including, but not limited to, frequency, pulse width, amplitude, waveform (e.g., square or sinusoidal), electrode polarity (i.e., anode-cathode assignment), location (i.e., which electrode pair or electrode group receives the stimulation current), burst pattern (e.g., burst on time and burst off time), duty cycle or burst repeat interval, spectral tilt, ramp-on time, and ramp-off time of the stimulation current that is applied to the stimulation site.

Figure 3:
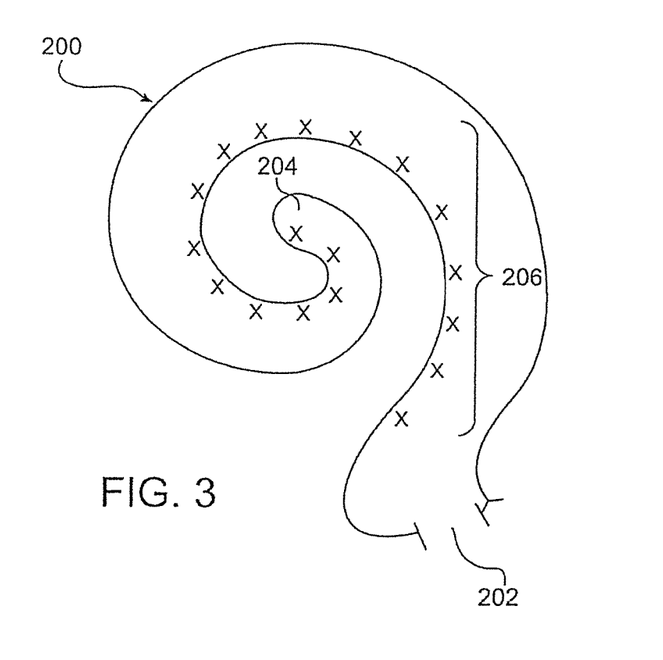
FIG. 3 is a schematic cross-section of a human cochlea with marked stimulation sites.

FIG. 3 illustrates a schematic structure of the human cochlea 200. As shown in FIG. 3, the cochlea 200 is in the shape of a spiral beginning at a base 202 and ending at an apex 204. Within the cochlea 200 resides auditory nerve tissue 206 which is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 12 is configured to apply stimulation to different locations within the cochlea 200 (e.g., different locations along the auditory nerve tissue 206) to provide a sensation of hearing.

Returning to FIG. 2, sound processing subsystem 11 and stimulation subsystem 12 is configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels and threshold current levels (as will be discussed in more detail below), input dynamic range parameters, channel acoustic gain parameters, front and backend dynamic range parameters, current steering parameters, amplitude values, pulse rate values, pulse width values, polarity values, filter characteristics, and/or any other control parameter as may serve a particular application. In particular, the control parameters may include a frequency allocation table (FAT) which determines the respective frequency range allocated to a certain electrode.

In the example shown in FIG. 2, the stimulation subsystem 12 comprises an implantable cochlear stimulator ("ICS") 14, a lead 16 and the stimulation assembly 18 disposed on the lead 16. The stimulation assembly 18 comprises a plurality of "stimulation contacts" 19 for electrical stimulation of the auditory nerve. The lead 16 may be inserted within a duct of the cochlea in such a manner that the stimulation contacts 19 are in communication with one or more stimulation sites within the cochlea, i.e. the stimulation contacts 19 are adjacent to, in the general vicinity of, in close proximity to, directly next to, or directly on the respective stimulation site.

In the example shown in FIG. 2, the sound processing sub-system 11 is designed as being located external to the patient 17; however, in alternative examples, at least one of the components of the sub-system 11 may be implantable.

In the example shown in FIG. 2, the sound processing sub-system 11 comprises a microphone 20 which captures audio signals from ambient sound, a microphone link 22, a sound processor 24 which receives audio signals from the microphone 20 via the link 22, and a headpiece 26 having a coil 28 disposed therein. The sound processor 24 is configured to process the captured audio signals in accordance with a selected sound processing strategy to generate appropriate stimulation parameters for controlling the ICS 14 and may include, or be implemented within, a behind-the-ear (BTE) unit or a portable speech processor ("PSP"). In the example of FIG. 2 the sound processor 24 is configured to transcutaneously transmit data (in particular data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within the ICS 14 in order to establish the link 30. The link 30 may include a bidirectional communication link and/or one or more dedicated unidirectional communication links. According to an alternative embodiment, the sound processor 24 and the ICS 14 may be directly connected by wires.

Figure 4:
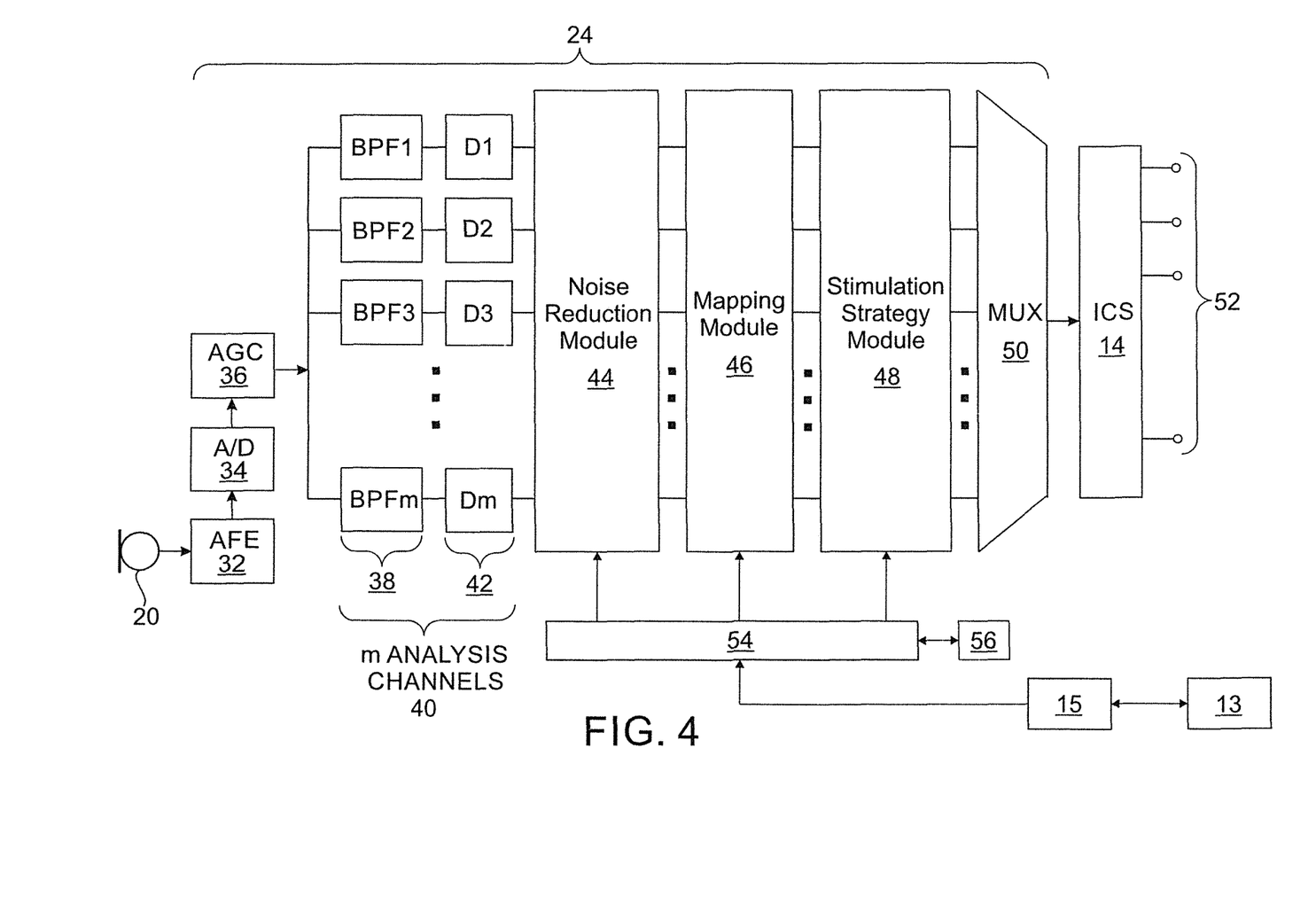
FIG. 4 is a block diagram of an example of the signal processing structure of a CI device to be used in the invention.

In FIG. 4 a schematic example of a sound processor 24 is shown. The audio signals captured by the microphone 20 are amplified in an audio front end circuitry 32, with the amplified audio signal being converted to a digital signal by an analog-to-digital converter 34. The resulting digital signal is then subjected to automatic gain control using a suitable automatic gain control (AGC) unit 36.

After appropriate automatic gain control, the digital signal is subjected to a filterbank 38 comprising a plurality of filters F1 . . . Fm (for example, band-pass filters) which are configured to divide the digital signal into m analysis channels 40, each containing a signal representative of a distinct frequency portion of the audio signal sensed by the microphone 20. For example, such frequency filtering may be implemented by applying a Discrete Fourier Transform to the audio signal and then distribute the resulting frequency bins across the analysis channels 40.

The signals within each analysis channel 40 are input into an envelope detector 42 in order to determine the amount of energy contained within each of the signals within the analysis channels 40 and to estimate the noise within each channel. After envelope detection the signals within the analysis channels 40 may be input into a noise reduction module 44, wherein the signals are treated in a manner so as to reduce noise in the signal in order to enhance, for example, the intelligibility of speech by the patient. Examples of the noise reduction module 44 are described in WO 2011/032021 A1.

The optionally noise reduced signals are supplied to a mapping module 46 which serves to map the signals in the analysis channels 40 to the stimulation channels S1 . . . Sn. For example, signal levels of the noise reduced signals may be mapped to amplitude values used to define the electrical stimulation pulses that are applied to the patient 17 by the ICS 14 via M stimulation channels 52. For example, each of the m stimulation channels 52 may be associated to one of the stimulation contacts 19 or to a group of the stimulation contacts 19.

The sound processor 24 further comprises a stimulation strategy module 48 which serves to generate one or more stimulation parameters based on the noise reduced signals and in accordance with a certain stimulation strategy (which may be selected from a plurality of stimulation strategies). For example, stimulation strategy module 48 may generate stimulation parameters which direct the ICS 14 to generate and concurrently apply weighted stimulation current via a plurality 52 of the stimulation channels S1 . . . Sn in order to effectuate a current steering stimulation strategy. Additionally or alternatively the stimulation strategy module 48 may be configured to generate stimulation parameters which direct the ICS 14 to apply electrical stimulation via only a subset N of the stimulation channels 52 in order to effectuate an N-of-M stimulation strategy.

The sound processor 24 also comprises a multiplexer 50 which serves to serialize the stimulation parameters generated by the stimulation strategy module 48 so that they can be transmitted to the ICS 14 via the communication link 30, i.e. via the coil 28.

The sound processor 24 may operate in accordance with at least one control parameter which is set by a control unit 54. Such control parameters, which may be stored in a memory 56, may be the most comfortable listening current levels (MCL), also referred to as "M levels", threshold current levels (also referred to as "T levels"), dynamic range parameters, channel acoustic gain parameters, front and back end dynamic range parameters, current steering parameters, amplitude values, pulse rate values, pulse width values, polarity values, the respective frequency range assigned to each electrode and/or filter characteristics. Examples of such auditory prosthesis devices, as described so far, can be found, for example, in WO 2011/032021 A1.

The fitting unit 13 may act on the control unit 54 via the interface 15 for causing the ICS 14 and the electrode array 19 to apply a certain probe stimulus to the cochlear 200 as will be discussed in detail below.

The hearing aid 21 comprises a microphone arrangement 29 for capturing audio signals from ambient sound, an audio signal processing unit 27 for processing the captured audio signals and the loudspeaker 23 to which the processed audio signals are supplied to. The fitting unit 13 may act, via the interface 15, on the audio signal processing unit 27 in order to cause the loudspeaker 23 to emit probe signals to be supplied to the contralateral ear.

Further, the fitting unit 13 may adjust the respective stimulation parameters via the interface 15 in order to change, for examples the I/O curves of the CI device 10 and the hearing aid 21.

The fitting unit 13 comprises a graphical user interface, which typically includes a screen 31. The fitting unit 13 allows the user to select between a HA-type fitting mode and a CI-type fitting mode, wherein each mode is suitable for fitting both the CI device 10 and the hearing aid 21. Preferably, the fitting unit 13 allows the user to select, as an alternative to the HA-type fitting mode and the CI-type fitting mode, a conventional fitting mode for fitting the CI device 10 in a CI-type manner and the hearing aid 21 in a HA-type manner.

According to a preferred embodiment, the system comprises a single fitting module for fitting both the CI device 10 and the hearing aid 21, i.e. there is a common fitting software running on the fitting unit 13 which communicates with both the CI device 10 and the hearing aid 21.

According to an alternative embodiment, there may be a first fitting module for fitting the CI device 10 and a second fitting module for fitting the hearing aid 21; such embodiment may be realized, for example, by a first fitting software communicating with the CI device 10 and a second fitting software communicating with the hearing aid 21, wherein both fitting software may run on the same hardware or they may run on dedicated separate hardware. Each fitting software allows the user to select at least between a HA-type mode and a CI-type mode for fitting of the device which communicates with the fitting software.

While in the example of FIG. 1 an electroacoustic hearing aid 21 comprising a loudspeaker 23 serves as the vibrational stimulation device of the bimodal stimulation system, in alternative embodiments the vibrational stimulation device could be a bone conduction hearing aid, a middle ear implant or a direct acoustic cochlear stimulator (DACS). Similarly, while in the example of FIG. 1 the neural stimulation device is a CI device comprising an implantable electrode array, in alternative embodiments neural stimulation device may be a CI device for optical cochlear stimulation or combined optical/electrical cochlear stimulation, or it may be an auditory brain stem implant.

While in the example of FIG. 1 the neural stimulation device is for neural stimulation of the ipsilateral ear and the vibrational stimulation device is for vibrational stimulation of the contralateral ear, in alternative embodiments the neural stimulation device and the vibrational stimulation device may be for bimodal stimulation of the same ear (such alternative embodiment is illustrated by dashed lines in FIG. 1, wherein a hearing aid 21 is integrated together with the CI device 10 within an EAS (electric acoustic stimulation) device 33).

The fitting mode switching feature of the present invention allows the user of the fitting unit to select that type of user interface, fitting controls and fitting workflow he or she is more familiar with, i.e. a hearing aid specialist is enabled to use a HA-type user interface, fitting controls and fitting workflow for fitting of both the hearing aid and the CI device, while a CI specialist is enabled to work with a CI-type user interface, fitting controls and fitting workflow for fitting of both the CI device and the hearing aid. Thus, for example, a CI specialist may continue or take over a patient from a hearing aid specialist. In particular, while the user interface and the controls may be completely different in the HA-type mode and the CI-type mode, the database entries, i.e. the fitting parameters which determine the fitting of the stimulation device, such as gain, T-levels, M-levels, etc., will be the same for the respective stimulation device, irrespective of whether the user uses a CI-type fitting mode or a HA-type fitting mode for fitting of the respective stimulation device. To this end, the fitting unit comprises a transformation layer for transforming an input from the user interface into fitting parameter values to be written to the respective stimulation device and for providing for an input to the user interface according to fitting parameter values read from the respective stimulation device.

The graphical user interface may provide for a single common screen for fitting both the neural stimulation device and the vibrational stimulation device, or it may provide for separate screens for fitting of the neural stimulation device and the vibrational stimulation device.

The user interface may be configured to display the output signal level of the neural stimulation device in a first unit, preferably in an electrode current unit, in both the HA-type fitting mode and the CI-type fitting mode, and to display the output signal level of the vibrational stimulation device in a second unit, preferably an acoustic unit like dB SPL or dB HL, in both the HA-type fitting mode and the CI-type fitting mode, wherein the two units are different.

In general, each of the neural stimulation device and the vibrational stimulation device comprises a plurality of stimulation channels, wherein the stimulation channels of the neural stimulation device are for neural stimulation of the patient's ipsilateral ear at various stimulation sites according to a neural stimulation signal, and the stimulation channels of the vibrational stimulation device are for vibrational stimulation of the patient's ipsilateral or contralateral ear according to an acoustic stimulation signal. In case that the neural stimulation device is a CI device including an implantable electrode array, each neural stimulation channel may correspond to a different one of the electrodes, with a certain frequency range of the input audio signal being mapped to the respective electrode. For the vibrational stimulation device the stimulation channels correspond to frequency bands of the acoustic stimulation signal. Typically, the neural stimulation device is used for stimulation in a higher frequency range, while the vibrational stimulation device is used for stimulation in a lower frequency range, with the two frequency ranges preferably having no overlap.

According to one example, the user interface may display the stimulation channels of the neural stimulation device and the stimulation channels of the vibrational stimulation device on a common screen; according to an alternative example, the stimulation channels of the neural stimulation device and the stimulation channels of the vibrational stimulation device may be displayed on separate screens.

The HA-type fitting mode typically includes the following features.

A stimulation perception threshold output level is measured in-situ for each neural and vibrational stimulation channel by recording patient feedback to an internally generated test output signal in the respective stimulation channel as a function of the output signal level. For the neural stimulation device thereby the frequency-specific T-levels (i.e. the output current required for creating a hearing perception) is determined for each electrode, while for the vibrational stimulation device in this step the frequency-specific hearing threshold (i.e. the sound pressure level required for creating a hearing perception) is determined in each frequency band. During the in-situ measurement the microphones are turned off, while the test signal is generated under control of the fitting unit (i.e. it may generated directly by the fitting unit or it may be generated by respective stimulation device upon request by the fitting unit). For the vibrational stimulation device the in-situ measurement step corresponds to the usual audiogram measurement, wherein the test signal may be a pure tone or narrow-band noise.

Based on the audiogram data and the T-levels determined in the threshold measurement step, stimulation parameters including gain (for the vibrational stimulation device) or stimulation signal output level, such as the M-levels (for the neural stimulation device) are pre-set by using an appropriate fitting formula (such as NAL-NL1 for hearing aids and AutoT for CI devices), so as to realize an initial fit ("first fit") as a starting point for subsequent fine-tuning. Such presetting may include M and T-level (i.e. the actual parameter derived from the behavioral M and T level) and parameters derived from considerations independent of individual behavioral thresholds, e.g. consideration which minimum sound pressure level (SPL) should be audible, like input dynamical range (IDR), sensitivity and input gain. It si noted that gain, more specifically: input gain, for a CI device is just one parameter which effects the I/O curve (output current vs. input sound pressure level) of the CI device—together with IDR and sensitivity.

In a fine-tuning step the microphones of the stimulation devices are turned on, so that the setting of the stimulation parameters can be evaluated based on the perception of audio signals captured by the stimulation device microphones. In the fine-tuning step, the user adjusts the output level of the vibrational stimulation device (which may be represented, for example, in "dB SPL") and the output current/charge of the neural stimulation device (in "CU" ("current units"), relating to the electrode current) for soft, medium and loud speech levels so as to fine-tune the frequency-specific gain values for both devices. The result of the fitting process may be displayed in a diagram showing the stimulation signal output level as a function of frequency for soft, medium and loud speech, together with behavioral threshold levels determined by the in-situ measurement step. In addition to the perception threshold output level also a measured most comfortable stimulation perception output level ("M-level") and a measured maximal tolerable stimulation perception output level ("clipping level") may be shown together with the gain/output level curves. The M-level and the clipping level for the neural stimulation device may be in-situ measured in a manner similar to the above-mentioned measurement of the T-level.

Figure 5:
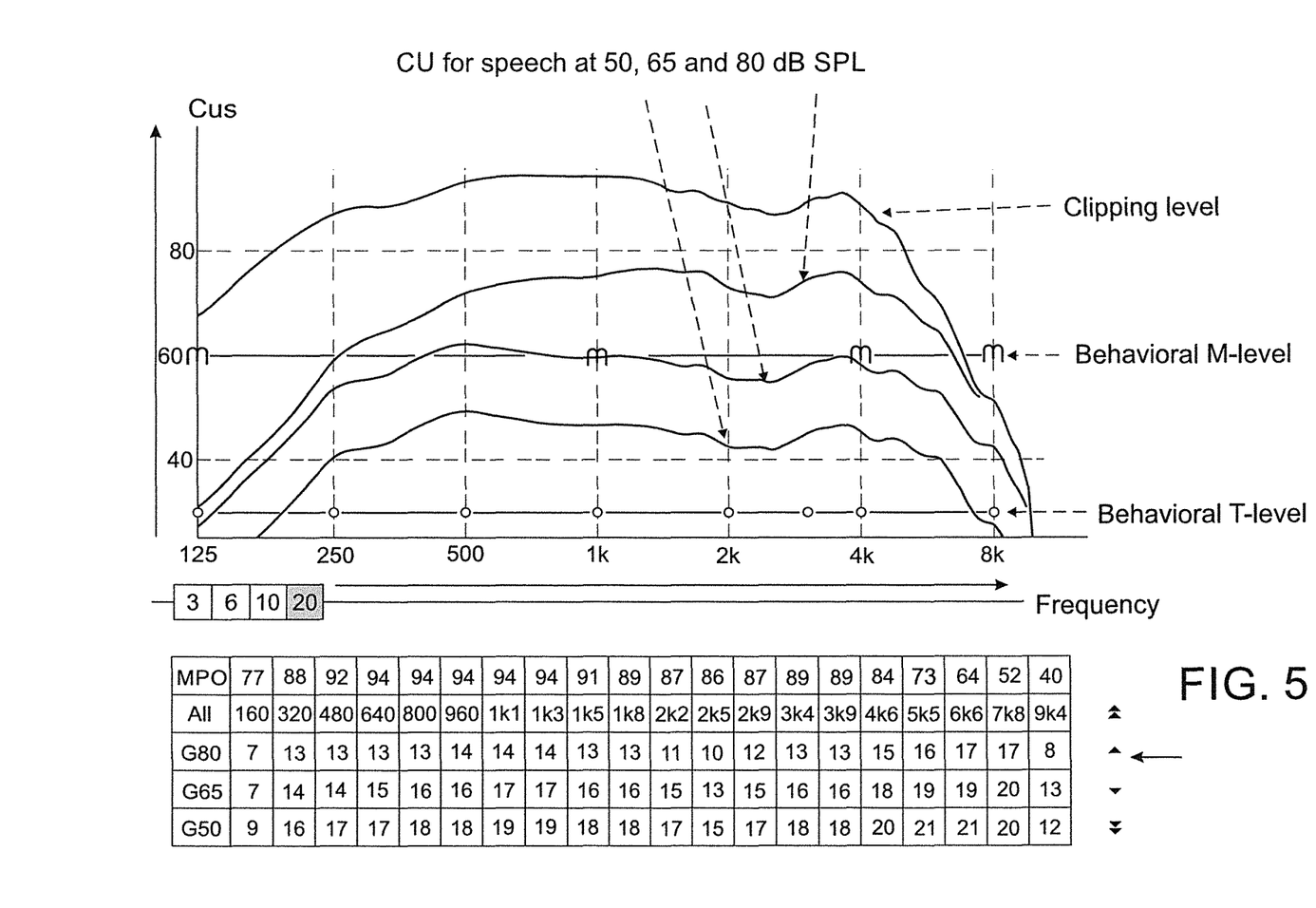
FIG. 5 is an example of a graphical user interface of a HA-type fitting mode when applied to a CI device.

An example of a graphical user interface in the HA-type fitting mode when used for fitting of a CI device is shown in FIG. 5, wherein the stimulation signal output level (in "CU") is shown as a function of frequency for speech input levels of 50, 65 and 80 dB SPL, respectively, together with the behavioral T-level, the behavioral M-level and the clipping level. The user interface allows for manual adjustment of the output level curves so as to provide for manual fine-tuning of the stimulation parameters as preset based on the measured T-level. While preferably the output curves are provided for three input speech levels, it also may be sufficient to provide the curves for only two speech input levels, for example for 50 and 80 dB SPL.

The automatic presetting of the stimulation parameters according to the fitting formula (which may be selectable by the user) for the neural stimulation device preferably comprises the setting of the M-level in each stimulation channel and the setting of the output level for at least two input sound levels.

For the vibrational stimulation device the automatic presetting may include setting of the gain and the compression parameters in all stimulation channels for at least two input sound levels.

Figure 8:
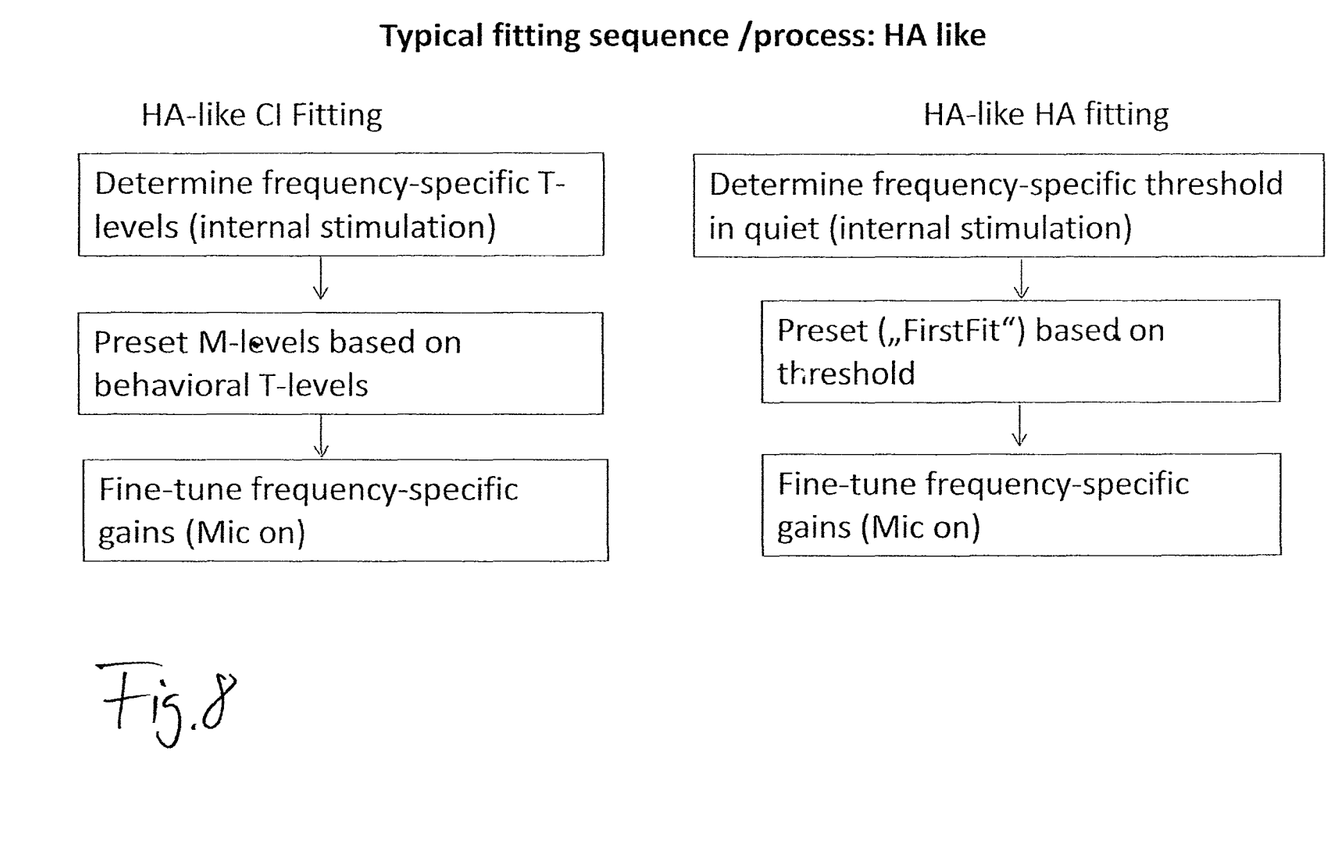
FIG. 8 is an example of a flow diagram for a HA-type fitting mode.

A schematic example of a workflow in the HA-type fitting mode for both the neural stimulation device and the vibration stimulation device is shown in FIG. 8.

The CI-type fitting mode typically includes the following features:

In a first step there is a manual coarse adjustment of the output signal in each neural and vibrational stimulation channel required for achieving a first global loudness perception and a second global loudness perception different from the first global loudness perception, wherein the output signal is an internally generated predetermined test signal, with the microphones of the stimulation devices being turned off ("global" in this regard means that the loudness perception is the same for all stimulation channels to which the loudness perception applies). Typically, the first global loudness perception is the stimulation perception threshold and the second global loudness perception is the most comfortable loudness perception (i.e. T-level and M-level, respectively). The test signal may be a tone or speech burst for the stimulation channels of the neural stimulation device and a pure tone or a narrow-band noise for the stimulation channels of the vibrational stimulation device.

Figure 6:
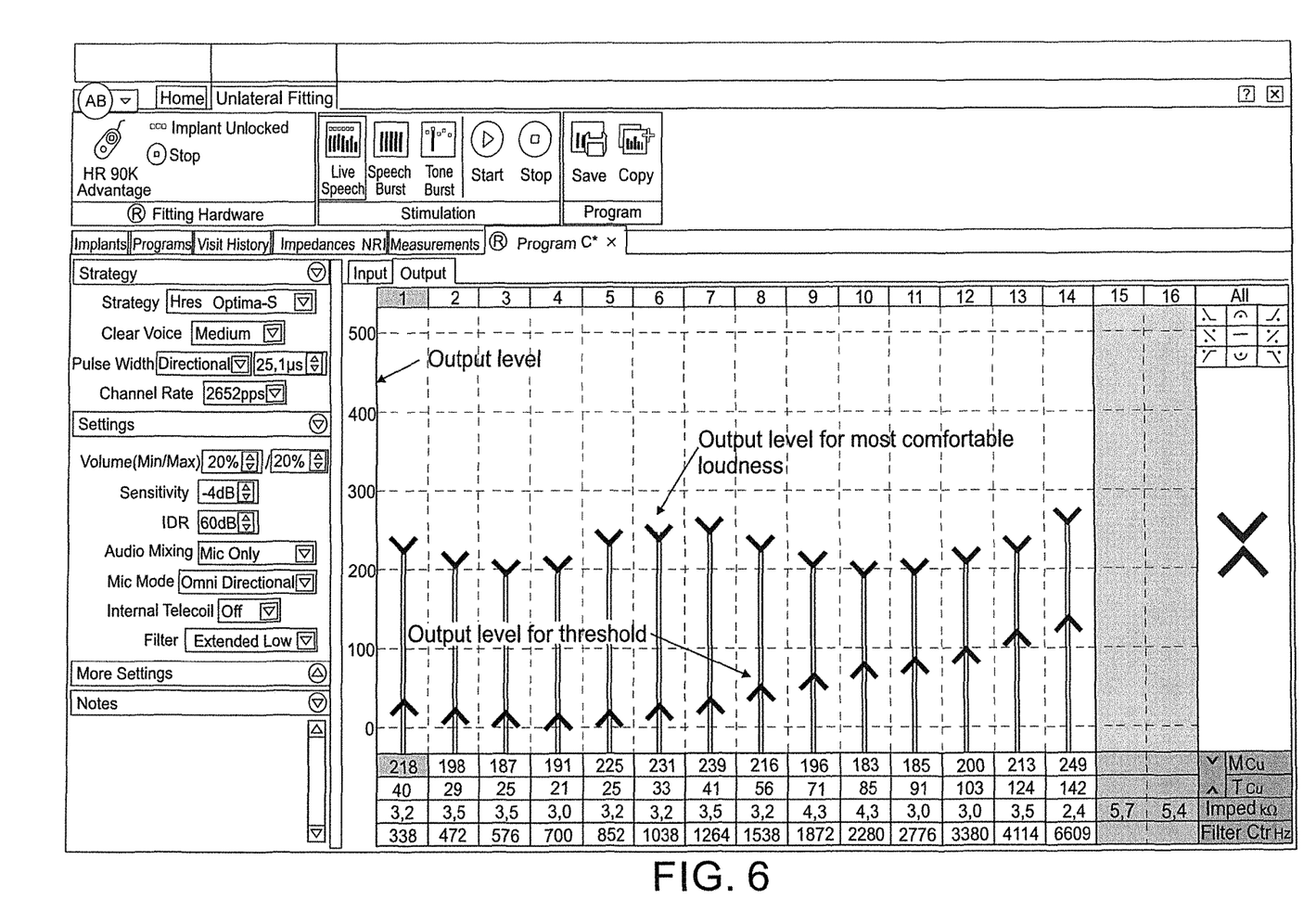
FIG. 6 is an example of a graphical user interface in a CI-type fitting mode when applied to an acoustic stimulation device.

An example of a graphical user interface in the CI-type fitting mode when used for fitting of a hearing aid is shown in FIG. 6; the graphical user interface offers the required controls for adjusting the M-output level and the T-output level for each stimulation channel. As illustrated in FIG. 6, the graphical user interface presents the presently set output signal level for the first global loudness perception and the second global loudness perception (usually T-level and M-level) in each stimulation channel as a function of the frequency (i.e. of the center frequency) of the stimulation channels.

Default values of operation parameters of the stimulation devices may be set at the end of the manual coarse adjustment based on the settings of the M-levels and T-levels obtained in by the coarse adjustment (such operation parameters may include IDR (input dynamic range, expansion, and AGC (automatic gain control) time constants).

When the coarse adjustment is finished, the fitting unit switches to fine adjustment, wherein the stimulation device microphones are turned on, so that the stimulation output signal now is generated from an audio signal captured by the stimulation device microphone(s) from ambient sound. At the beginning of the fine adjustment step a global adjustment of the output signal levels in all stimulation channels may take place (i.e. there is the same change of the output level for all stimulation channels of the respective stimulation device); in the example of FIG. 6 the T-levels and M-levels would be changed in the same manner for all stimulation channels. This global adjustment of the output levels is based on the patient feedback to the stimulation signals generated from input audio signals captured by the microphone(s).

This global adjustment step is followed by a fine adjustment step in which the respective output levels (such as the M-level) are individually adjusted for each stimulation channel based on patient feedback to the stimulation signals generated from the input audio signals captured by the microphone(s).

In the manual fine adjustment step of the CI-type fitting mode, when applied to the vibrational stimulation device, a definition is required which specifies the acoustic levels which are connected to the respective T- and M-level; for example, the T-level may correspond to soft speech or threshold input level in quiet for normal hearing listeners, and the M-level may correspond to speech at a level of 63 dB SPL. Additionally, adjustments of the T-level and the M-level on output level need to be converted into gain changes, wherein the gain (in logarithmic units) is output (as displayed/adjusted)–input (as specified). Such conversion is provided by the transformation layer of the fitting unit.

Figure 9:
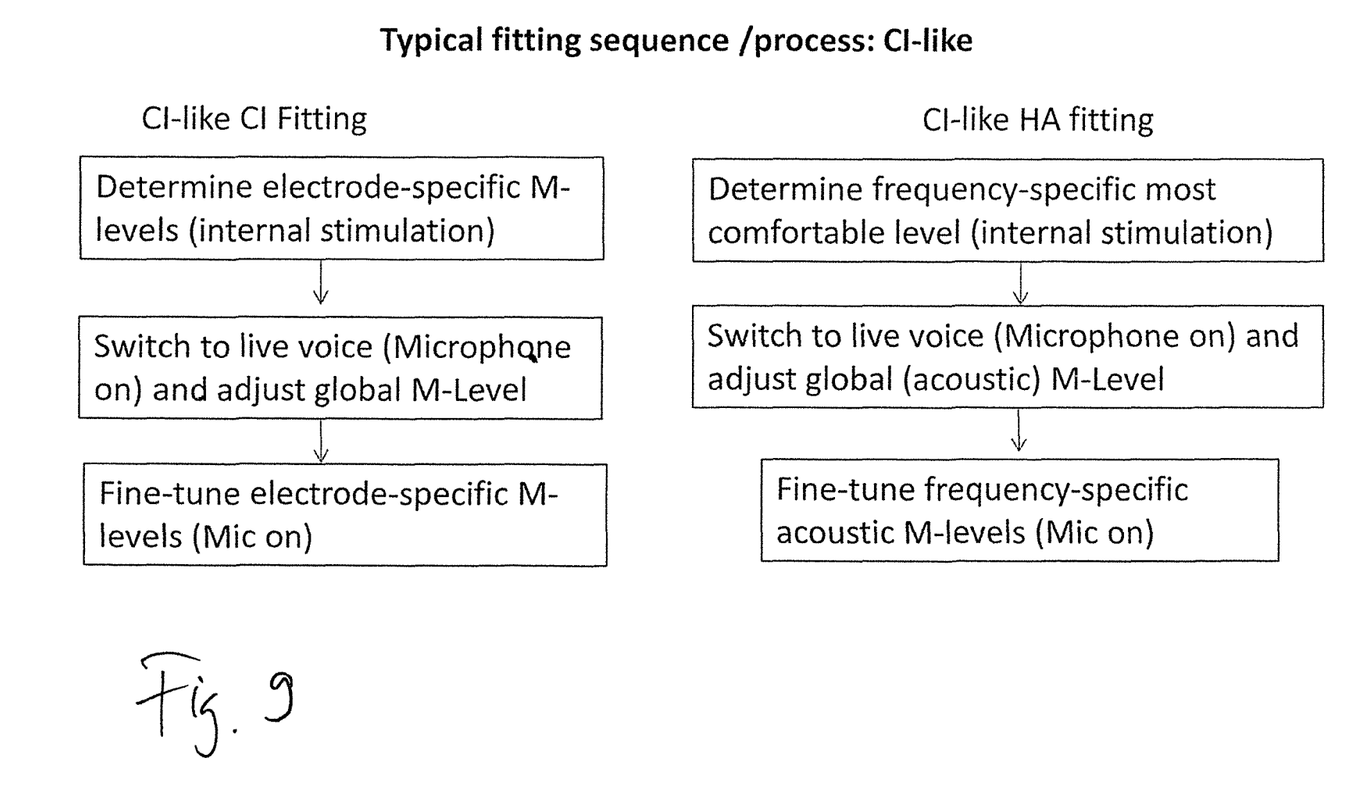
FIG. 9 is an example of a flow diagram for a CI-type fitting mode.

A schematic example of a workflow in the CI-type fitting mode for both the neural stimulation device and the vibration stimulation device is shown in FIG. 9.

A schematic example of a workflow in a conventional fitting mode is shown in FIG. 7, wherein the HA-type fitting of FIG. 8 is applied only for the vibration stimulation device and the CI-type fitting of FIG. 9 is applied only for neural stimulation device.

The invention claimed is:

1. A fitting device configured to be communicatively connected to a first stimulation device comprising an implantable electric stimulation device including a plurality of stimulation channels for electrical stimulation of a patient's ipsilateral ear at various stimulation sites according to a electrical stimulation signal and a second stimulation device selected from the group consisting of a device for acoustic stimulation of the patient's ipsilateral ear and a device for acoustic stimulation of the patient's contralateral ear according to an acoustic stimulation signal for adjusting the first stimulation device and the second stimulation device;

the fitting device comprising a graphical user interface and being configured to allow a user to select between a HA-type fitting mode and a CI-type fitting mode,
wherein the fitting device is configured to provide, in the HA-type fitting mode, for
in-situ measurement of a stimulation perception threshold output level for electrical and acoustic stimulation channels by recording patient feedback to a test output signal in the respective stimulation channel as a function of the output signal level;

presetting of stimulation parameters including gain and/or a stimulation signal output level based on the measured stimulation perception threshold output levels; and manual fine-tuning of stimulation parameters including gain and/or the stimulation signal output level;

wherein the fitting device is configured to direct the graphical user interface to present gain and/or stimulation signal output level in the stimulation channels for at least two different sound input levels and to allow for manual adjustment of the presented gain and/or stimulation signal output level in the stimulation channels for said at least two different sound input levels;

wherein the fitting device is configured to provide, in the CI-type fitting mode, for:

manual coarse adjustment of the output signal level in the electrical and acoustic stimulation channels required for achieving at least one global loudness perception, wherein the output signal is a predetermined test signal; and manual fine adjustment of the output signal level in the electrical and acoustic stimulation channels required for achieving the at least one global loudness perception, wherein the stimulation output signal is generated from an audio signal captured by a microphone from ambient sound;

wherein the fitting device is configured to direct the graphical user interface to present the presently set output signal level for the at least one global loudness perception in the stimulation channels as a function of a center frequency of the stimulation channels; and wherein the fitting device comprises a transformation layer for transforming an input from the graphical user interface into fitting parameter values to be written to the stimulation devices and for providing for an input to the graphical user interface, the input to the graphical user interface comprising fitting parameter values read from the stimulation devices.

2. The device of claim 1, wherein the fitting device is configured to allow the user to select, as an alternative to the HA-type fitting mode and the CI-type fitting mode, a conventional fitting mode for fitting the first stimulation device in a CI-type manner and the second stimulation device in a HA-type manner.

3. The device of claim 1, wherein the fitting device is configured to direct the graphical user interface to display the output signal level of the first stimulation device in a first unit in both the HA-type fitting mode and the CI-type fitting mode and to display the output signal level of the second stimulation device in a second unit in both the HA-type fitting mode and the CI-type fitting mode, wherein the second unit is different from the first unit.

4. The device of claim 3, wherein the fitting device is configured to direct the graphical user interface to display, in both the HA-type fitting mode and the CI-type fitting mode, the output signal level of the first stimulation device in an electrode current unit and the output signal level of the second stimulation device in an acoustic unit.

5. The device of claim 1, wherein the fitting device is configured to direct the graphical user interface to display the stimulation channels of the first stimulation device and the stimulation channels of the second stimulation device on a common screen.

6. The device of claim 1, wherein the fitting device is configured to direct the graphical user interface to display the stimulation channels of the first stimulation device and the stimulation channels of the second stimulation device on separate screens.

7. The device of claim 1, wherein the fitting device is configured to direct the graphical user interface to display, in the HA-type fitting mode, for the stimulation channels of the first stimulation device, together with the gain and/or stimulation signal output level, at least one of the measured stimulation perception threshold output level, a measured most comfortable stimulation perception output level and a measured maximal tolerable stimulation perception output level.

8. The device of claim 1, wherein the fitting device is configured to direct the graphical user interface to display, in the HA-type fitting mode, for the stimulation channels of the first stimulation device, the respective stimulation signal output level for said at least two different sound input levels.

9. The device of claim 1, wherein the fitting device is configured to measure, for the stimulation channels of the first stimulation device, a most comfortable stimulation perception output level by recording patient feedback to the test output signal in the respective stimulation channel as a function of the test signal output level.

10. The device of claim 1, wherein the fitting device is configured to measure, for the stimulation channels of the first stimulation device, maximal tolerable stimulation perception output level by recording patient feedback to the test output signal in the respective stimulation channel as a function of the test signal output signal level.

11. The device of claim 1, wherein the presetting of stimulation parameters comprises setting of the gain and/or the output level as a function of the sound input level in the stimulation channels.

12. The device of claim 1, wherein the presetting of stimulation parameters comprises setting of the most comfortable level in the stimulation channels.

13. The device of claim 1, wherein the fitting device is configured to direct the graphical user interface to present, in the HA-type fitting mode, for a low sound input level, a medium sound input level and a high sound input level, gain and/or stimulation signal output level and to allow for manual adjustment of the presented gain and/or stimulation signal output level in the stimulation channels.

14. The device of claim 1, wherein the fitting device is configured to use, in the fine-tuning of stimulation parameters fine-tuning in the HA-type fitting mode, a stimulation output signal which is generated from an audio signal captured by a microphone of the first and/or second stimulation device from ambient sound.

15. The device of claim 1, wherein the at least one global loudness perception is the most comfortable stimulation perception.

16. The device of claim 1, wherein the at least one global loudness perception includes a first global loudness perception and a second global loudness perception different from the first global loudness perception.

17. The device of claim 16, wherein in the CI-type fitting mode the first global loudness perception is the stimulation perception threshold and the second global loudness perception is the most comfortable stimulation perception.

18. The device of claim 1, wherein the second stimulation device is the device for acoustic stimulation of the patient's contralateral ear.

19. The device of claim 1, wherein the second stimulation device is the device for acoustic stimulation of the patient's ipsilateral ear.

20. A method of fitting a first stimulation device comprising an implantable electric stimulation device including a plurality of stimulation channels for electrical stimulation of a patient's ipsilateral ear at various stimulation sites according to a electrical stimulation signal and a second stimulation device selected from the group consisting of a device for acoustic stimulation of the patient's ipsilateral ear and a device for acoustic stimulation of the patient's contralateral ear according to an acoustic stimulation signal, comprising:
- communicatively connecting a fitting device comprising a graphical user interface to the first stimulation device and to the second stimulation device;
- allowing a user to select between a HA-type fitting mode and a CI-type fitting mode,
- wherein the fitting device provides, in the HA-type fitting mode, for
  - in-situ measurement of a stimulation perception threshold output level for electrical and acoustic stimulation channels by recording patient feedback to a test output signal in the respective stimulation channel as a function of the output signal level;
  - presetting of stimulation parameters including gain and/or a stimulation signal output level based on the measured stimulation perception threshold output levels; and
  - manual fine-tuning of stimulation parameters including gain and/or the stimulation signal output level;
  - wherein the fitting device directs the graphical user interface to present gain and/or stimulation signal output level in the stimulation channels for at least two different sound input levels and to allow for manual adjustment of the presented gain and/or stimulation signal output level in the stimulation channels for said at least two different sound input levels;
- wherein the fitting device provides, in the CI-type fitting mode, for:
  - manual coarse adjustment of the output signal level in the electrical and acoustic stimulation channels required for achieving at least one global loudness perception, wherein the output signal is a predetermined test signal; and
  - manual fine adjustment of the output signal level in the electrical and acoustic stimulation channels required for achieving the at least one global loudness perception, wherein the stimulation output signal is generated from an audio signal captured by a microphone from ambient sound;
  - wherein the fitting device directs the graphical user interface to present the presently set output signal level for the at least one global loudness perception in the stimulation channels as a function of a center frequency of the stimulation channels; and
- wherein an input from the graphical user interface is transformed into fitting parameter values written to the stimulation devices and an input to the graphical user interface is provided, the input to the graphical user interface comprising fitting parameter values read from the stimulation devices.

* * * * *